United States Patent [19]

Fujii et al.

[11] 3,932,618

[45] Jan. 13, 1976

[54] ANTI-INFLAMMATORY COMPOSITIONS

[75] Inventors: Setsuro Fujii, Tokushima; Masatomi Otsuka, Naruto; Yoshiyasu Osaki, Tokushima, all of Japan

[73] Assignee: Otsuka Kagaku Yakuhin Kabushiki Kaisha, Japan

[22] Filed: Apr. 14, 1972

[21] Appl. No.: 244,256

[30] Foreign Application Priority Data

Apr. 14, 1971 Japan.............................. 46-24004

[52] U.S. Cl.................................. 424/94; 424/101
[51] Int. Cl.² .................. A61K 35/14; A61K 37/48
[58] Field of Search ........ 424/94, 101; 195/DIG. 11

[56] References Cited

UNITED STATES PATENTS 3,004,893   10/1961   Martin .................................. 424/94

Primary Examiner—Jerome D. Goldberg
Assistant Examiner—D. W. Robinson
Attorney, Agent, or Firm—Armstrong, Nikaido & Wegner

[57] ABSTRACT

An anti-inflammatory composition comprises an anti-inflammatorily effective amount of a reaction product of a blood with a protease.

8 Claims, No Drawings

ANTI-INFLAMMATORY COMPOSITIONS

This invention relates to a novel and useful anti-inflammatory composition and a process for producing an anti-inflammatory substance.

Various anti-inflammatory substances have heretofore been used, for example, such as steroids like cortisone, dexamethasone; nonsteroids like anthranilic acid derivatives, solicylates, indomethacin, benzydamine; gold sols; and proteases. Because of considerable side effects, however, it has been difficult to use these conventional substances in doses sufficient to produce satisfactory anti-inflammatory activities. For instance, the present inventors conducted inhibition tests on edema caused by carrageenin using various proteases through intraperitoneal administration, the most usual method of administration employed at present, whereby it was found that although each of the proteases produced an appreciable inhibitive effect on edema, an increased dosage for improved effect caused bleeding in the abdominal cavity or ascites. This indicates that each protease has to be administered within a permissible range of dosage to prevent side effects. Such tendency was found with respect to various proteases. Examples of the proteases are trypsin, chymotrypsin and the like from animal sources; bromelin, papain and the like from vegetable sources; and those obtained from microorganisms such as Streptomyces griseus, Bacillus subtilis, Aspergillus melleus, Aspergillus niger and other bacteria of Genus Serratia and Genus Bacillus.

Accordingly, an object of this invention is to provide an anti-inflammatory substance capable of producing excellent anti-inflammatory activities and substantially free of side effects.

Another object of this invention is to provide an anti-inflammatory substance capable of giving high anti-inflammatory activities in a small dose and free of side effects such as bleeding and ascites even when administered at a high concentration.

Another object of this invention is to provide an excellent anti-inflammatory composition containing the above-mentioned anti-inflammatory substance as an effective component thereof.

Still another object of this invention is to provide a process for producing an anti-inflammatory substance from proteases, said anti-inflammatory substance exhibiting higher anti-inflammatory activities free from any harmful effect as compared with proteases having the foregoing drawbacks.

These and other objects and advantages of the invention will be apparent from the following description.

The anti-inflammatory composition of the invention comprises an anti-inflammatorily effective amount of a reaction product of blood with a protease and an adjuvant.

Throughout the specification and claims the word "blood" means not only blood itself but also substances obtained from blood per se, such as blood plasma, blood serum, etc.

The researches by the present inventors have indicated that a substance obtained by the reaction of blood with protease (the substance being hereinafter referred to as a "modified blood substance") gives very high anti-inflammatory effects in a small dose substantially free of harmful effect and produces hardly any harmful effects even when administered in high doses. These effects which have never been achieved with proteases are assured only through the modification of blood by the enzymatic action of protease. Indeed, this will be apparent from Table 1 below showing inhibition effects on edema of the modified blood substance according to this invention in comparison with those of various proteases. The modified blood substance tested was obtained in the same manner as in the appended Example 1 by reacting a cow serum with a protease obtained according to the method of U.S. Ser. No. 868,613 from Bacillus sp 0 – 20 (Deposited at Fermentation Research Institute of Agency of Industrial Science and Technology, Japan, since Feb. 20, 1969, with Deposition number of FERM-P 270, product of Otsuka Kagaku Yakuhin Kabushiki Kaisha, Osaka, Japan) and removing unreacted protease from the resulting reaction product.

Test method for 50 percent inhibition on edema

Various anti-inflammatory agents shown in Table 1 below were respectively dissolved or dispersed in physiological saline and intraperitoneally administered to one group of six rats weighing 150 to 160 g. In 30 minutes 0.05 ml of 1 wt.% carrageenin dissolved in physiological saline was subscutaneously injected in the sole of rear foot of each rat. Increase of volume of the rear foot was measured in 3 hours thereafter to determine inhibitive effect on edema. 50 percent inhibition is shown in terms of doses ($\gamma$/kg) required therefor. In this test physiological saline was used as a control.

Doses Required for 50 percent Inhibition of Edema

Table 1

| Anti-inflammatory agents tested | $ED_{50}$ $\gamma$/kg |
| --- | --- |
| Modified blood substance of Ex. 1 | 50 |
| Protease produced from Bacillus sp 0 – 20 | 1,000 |
| Bromelain | 10,000 |
| Indomethacin | 2,300 |
| Mefenamic acid | 9,100 |
| Flufenamic acid | 10,500 |
| Phenylbutazone | 24,000 |
| Phenacetin | 60,000 |
| Aspirin | 73,000 |
| Cinchophene | 92,000 |

It will be seen from Table 1 that the modified blood substance of this invention produces excellent anti-inflammatory activities at much smaller dose than various proteases compared. It is to be noted that 50 percent inhibition on edema by the protease obtained from Bacillus sp 0 – 20 can be achieved by the modified blood substance prepared therefrom in an amount as small as 1/20 the amount of the former.

Moreover, the substance of this invention is free from side effects, entirely harmless at such low concentration and gives hardly any side effects when administered at high doses. In fact, when for instance intraperitoneally given to a rat at a high dose of 500,000 $\gamma$/kg, the modified blood substance obtained in Example 1 did not produce any side effects such as intraperitoneal bleeding or ascites.

Furthermore, the modified blood substance of this invention which exhibits the foregoing outstanding anti-inflammatory activities has hypotensive action and depressive action on the central nervous system. Thus by utilizing such pharmacological actions, it is possible to obtain such effects as heretofore unavailable with the conventional anti-inflammatory enzymatic agents.

The modified blood substance of this invention is a substance obtained by modification of blood with a protease and is soluble in water but insoluble in methanol. It is a liquid to solid substance containing peptide, amino acid and sugar.

The modified blood substance of the invention is substantially different from blood in view of that the former displays a high order of anti-inflammatory effect whereas the latter exhibits no such effects. Further, the modified blood substance of the invention exhibits no enzymatic activity, thus substantially different from protease.

The blood to be used as a starting material of this invention includes blood per se, blood plasma, blood serum and various substances obtained from blood per se of mammals such as man, rabbit, rat, cow, horse, birds such as hen, duck and a wide variety of animals, of which particularly preferable are blood per se and blood serum of mammals. Because of easy availability, blood per se and blood serum of cow and horse are most preferable.

The protease for modifying the blood includes various proteases obtained from animals, vegetables and microorganisms. Examples are those of animal sources such as trypsin, pepsin, chymotrypsin, pancreatin, etc.; those of vegetable sources such as bromelin, papain, etc.; those of microorganisms such as filamentous fungus, basidiomycetes, bacterium, ray fungus, etc. Proteases obtained from filamentous fungus are, for example, those from *Aspergillus melleus, Aspergillus oryzae, Penicillium notatum, Rhizopus chinensis, Mucor racemosus*, etc. Proteases from basidiomycetes are those from *Trametes sanguinea, Llodella subpileata*, etc. Proteases from bacterium are those from *Bacillus subtilis, Pseudomonas myxogenes*, etc. Proteases from ray fungus are those from *Streptomyces griseus, Streptomyces fradiase*, etc. Among these proteases, chymotrypsin, bromelin and proteases from *Bacillus subtilis* and *Aspergillus melleus* are preferred. Further in place of protease per se, also employable are substances prepared by chemically modifying proteases in known manner. For this purpose, protease is chemically modified by reacting a high molecular weight substance such as polymers of amino acid and polysaccharides with protease by diazotization, peptidation, dehydrogen halide reaction, etc., by reacting such a high molecular weight substance having ion-exchange group with protease, or by cross linking $\epsilon$-amino group of lysine of enzyme or $\alpha$-amino group at the end of N atom thereof or phenol group of tyrosine or enzyme or SH of systein thereof with such a high molecular weight substance having at least two functional groups. As examples of specific polymers which are suitable for use in the invention are those disclosed in the present applicants' copending application, Ser. No. 244,255 now abandoned, filed on even date herewith, and claiming priority of Japanese Pat. application No. 24005/71, filed Apr. 14, 1971. Methods for the chemical modification of proteases have been described in "Nature" 210, No. 23, by Rolf Axen and Jerker Porath, in "The Journal of Biological Chemistry" 237, No. 6, P. 1832–1838 (1962) in Japanese Pat. Publication No. 27492/1964, in U.S. Pat. No. 3,167,485, and in "Seventeenth Collection of Lectures at Enzyme Chemistry Symposium," P. 21 (1965) by Toru Takami and Toshio Ando. This symposium was staged at Tokushima University, Japan on May 2nd to 5th, 1965.

In accordance with the invention the modification of blood by protease is usually conducted at room temperature or at a moderately elevated temperature, preferably at 20° to 60°C. Generally pH of the reaction system depends on the type of blood and protease used, but most preferably it is at neutral. The amount of protease relative to blood which may also be dependent on the kind of protease and blood is preferably 200 to 2,000 $\gamma$ per ml of the blood. The reaction is generally completed within 0.5 to 5 hrs. to give a modified blood substance.

The resulting modified blood substance is separated for recovery from unreacted protease and unreacted blood, if any, for example, by using an organic solvent, molecular sieve, ion exchange resin, centrifuge, counter current distribution method, electrophoresis method or other known methods. These methods may be used singly or in combination. It is not necessary to remove unreacted protease from the reaction mixture if it is in a small amount. Further, instead of separation, the unreacted protease may be inactivated by physical or chemical means as by heating. In some cases, the unreacted blood need not be removed from the resulting product.

The modified blood substance of this invention is in the form of liquid to solid and is made into various forms in usual method for administration as an anti-inflammatory agent. For example, it may be dissolved in physiological saline to provide the same in the form of a solution, or it may be made into tablets, granules or powder in usual method. In the preparation of tablets and granules, as adjuvants are preferably employed (a) lactose, starch and similar excipients; (b) methyl cellulose and like glossing agents; and (c) talc and like binding agents. In the preparation of powder, lactose, starch, talc, etc., can be used as adjuvants. Alternatively, it may be prepared as an ointment in the conventional method. In ointments, acacia, glycerin, etc., may be used as adjuvants. Depending upon the form of preparation, it may be administered intraperitoneally, orally or applied locally.

For a better understanding of this invention, examples are given below.

EXAMPLE 1

To 10 liters of blood serum of cow was added 1 g of protease obtained according to the method of U.S. Ser. No. 868,613 from bacteria of Bacillus sp 0 – 20. The protease used in this Example has a proteolytic activity of 4,000,000 PU/g. The proteolytic activity shows enzymatic activity of the protease producing nonprotein substance showing folin colour corresponding to 1 $\gamma$ of tyrosine in one minute as one unit of enzymatic activity. The mixture was heated at 45°C for 4 hours in a constant temperature water bath. Acetone was added to the reaction mixture to 70 wt.% and the resulting mixture was centrifuged at 3,000 r.p.m. for 10 minutes to separate off the enzyme, protein, etc., which were removed in the form of precipitate. Acetone was added to the supernatant to 90 wt.% and the mixture was left to stand for 1 day. The resulting precipitate was recovered by centrifuging at 3,000 r.p.m. over a period of 30 minutes and dried in a vacuum. The recovered product was dissolved in water and subjected to gel filtration with "Sephadex G-15" (Trade mark, dextran of Pharmacia Fine Chemicals, Sweden) to remove inorganic substances and lower molecular weight substances. The edema inhibitive portion of the product, as ascertained by testing on edema in the heel of rat was freeze-dried, and further washed with methanol thoroughly to completely remove a methanol soluble material. By removing methanol from the methanol insoluble portion, 25 mg of a modified blood substance was obtained in solid state. The composition of this substance is as follows:

| Composition | Content |
| --- | --- |
| Amino acid *1 (calculated as leucine) | 14 wt. % |
| Amino acid *2 (calculated as leucine) | 70 wt. % |
| Sugar (calculated as glucose) | 12 wt. % |

Note:
*1 Amount of amino acid determined by ninhydrin reaction of the substance.
*2 Amount of amino acid determined by ninhydrin reaction of the substance hydrolyzed with 6N HCl at 110°C for 36 hours.

The composition of principal amino acid is:

| Amino acids | Content |
| --- | --- |
| Aspartic acid | 7 wt.% |
| Glutamic acid | 8 wt.% |
| Glycine | 3 wt.% |

The substance was dissolved in physiological saline in a contentration of 8 $\gamma$/ml and intraperitoneally administered to rats weighing 150 to 160 g. In 30 minutes 0.05 ml of 1 wt.% carrageenin dissolved in physiological saline was subscutaneously injected in the sole of rear foot of each rat. Increase of volume of the rear foot was measured 3 hours thereafter to determine inhibitive effect on edema. Thus it was found that a dose of 8 $\gamma$/150 g (body weight of rat) achieved 60 percent inhibition on edema. No intraperitoneal bleeding and ascites took place.

For comparison, the protease used in this example was intraperitoneally administered to rats in the same manner as above. In 3 hours after administration, only 5 percent of inhibition on edema was attained at a dose of 8 $\gamma$/150 g. A dose of 170 $\gamma$/150 g resulted in 60 percent inhibition on edema, with marked intraperitoneal bleeding.

EXAMPLE 2

To 5 ml of blood serum of rat was added 2 mg of protease (proteolytic activity of 4,000,000[PU]/g, determined in the same manner as in Example 1) obtained from Bacillus sp 0 - 20 as in Example 1 and the mixture was shaken for 1 hour in a constant temperature water bath at 37°C. The product thus obtained was heated at 60°C for 2 hours to completely inactivate the enzyme, whereby a modified blood substance of this invention was obtained in a crude state. The substance contained peptide, amino acid and sugar and was soluble in water.

The modified blood substance was dissolved in physiological saline in a concentration of 400 $\gamma$/ml and then intraperitoneally given to rats weighing 150 to 200 g at a dose of 1 ml/200 g (body weight of rat) to examine its inhibitive effect on edema produced by subcutaneous injection of carrageenin in the heel of rear foot of the rat. In 3 hours after administration, 65 percent inhibition on edema was achieved at a dose of 400 $\gamma$/200 g as determined by measuring the volume of the rear foot. There was no sign of intraperitoneal bleeding. In contrast, no inhibitive effect on edema was achieved when a serum which had not been modified with protease was administered in the same manner as above. The starting protease on edema was measured in the same manner as above. Thus it was found that intraperitoneal bleeding was observed at a dose of 400 $\gamma$/200 g, while 64 percent inhibitive effect was attained.

EXAMPLE 3

5 mg of bromelin was reacted with 5 ml of human serum at 35°C for 1.5 hours, and the reaction mixture was then cooled to 3°C. Cold acetone of 3°C was then added to the mixture to a concentration of 60 wt.%, this being followed by freeze-centrifuging to remove bromelin. The product thus obtained exhibited no proteolytic activities. Removal of acetone from the product under a reduced pressure resulted in 2.5 mg of crude modified blood substance which was consistent and light yellowish and contained peptide, amino acid and sugar. The substance was soluble in water.

The modified blood substance was then dissolved in physiological saline in a concentration of 0.5 mg/ml, which was intraperitoneally given to a rat at a rate of 1 ml/200 g (body weight of rat) to examine its inhibitive effect on edema produced by subcutaneous injection of dextran in the heel of rear foot of the rat. In 3 hours, 70 percent inhibition on edema was achieved. There was no sign of intraperitoneal bleeding. In contrast, no inhibitive effect on edema was attained when a blood serum which had not been reacted with protease was given in the same manner as above. Inhibitive effect of the starting bromelin on edema was tested in the same manner as above. Thus 55 percent inhibition was attained with marked intraperitoneal ascites.

EXAMPLE 4

With 1000 ml of cow blood containing sodium citrate added thereto as an anti-coagulating agent was reacted 1 g of protease (trademark "Nagase," product of Nagase Sangyo Co., Ltd., Osaka, Japan) obtained from *Bacillus subtilis* at 37°C for 2 hours. Acetone was added at 10°C to the blood thus treated to a concentration of 60 wt.%, and the resulting mixture was freeze-centrifuged to remove blood sediment, enzyme, etc. The supernatant obtained was found free of enzymatic activities. Cold acetone was further added to the supernatant to a concentration of 80 wt.%, and the precipitate was recovered by freeze-centrifuging, which was found to contain peptide, amino acid and sugar and to be soluble in water.

The whole amount of the modified blood substance thus obtained was dissolved in 10 ml physiological saline and the resulting solution was further diluted with physiological saline to 5 times, 10 times and 100 times the original amount. The original solution and diluted solutions were intraperitoneally given to rats at a rate of 1 ml/200 g (body weight of rat) to examine the inhibitive effect on edema produced by subcutaneous injection of carrageenin in the heel of rear foot of each rat. The inhibition achieved in 3 hours after administration was; 80 percent with the original solution, 62 percent with five times dilution; 53 percent with 10 times dilution, and 51 percent with 100 times dilution. No adverse effects such as intraperitoneal bleeding and ascites were found. In contrast, no inhibitive effect was found when blood which had not been modified with protease was given in the same manner as above. Further Nagase (Trade mark, the same as above) was likewise given to determine inhibitive effect on edema. 40 percent inhibition was attained at a dose of 1 mg/200 g (body weight of rat) and increase of dose to 1.2 mg/200 g (body weight of rat) gave 51 percent inhibition, causing marked intraperitoneal bleeding.

EXAMPLE 5

"Semialkali protease", (Trade mark, product of Seikagaku Kogyo Co., Ltd., Tokyo, Japan) obtained from aspergillus melleus was reacted with 1 liter of cow serum under the condition of 500[PU]*/ml (serum) at 30°C for 1 hour. Acetone was then added to the serum thus treated to 70 wt.% and the mixture was centrifuged at 3,000 r.p.m. for 20 minutes, followed by removal of resulting sediment and further addition of acetone to 95 wt. %. The mixture thus prepared was left to stand for a day and centrifuged at 3,000 r.p.m. for 30 minutes. The modified blood substance was then recovered and vacuum-dried to obtain 2.9 g of brown powder, which was found free of proteolytic activities. The substance contained peptide, amino acid and sugar and was soluble in water but insoluble in methanol.

*: The amount of trichloroacetic acid soluble substance corresponding to 1 γ /min of tyrosine produced at 30°C.

The resultant substance was dissolved in physiological saline and inhibitive effect of the substance on rats was tested in the same manner as in Example 1. 54 percent inhibition was achieved at a dose of 290 mg/kg. There was no sign of intraperitoneal bleeding and ascites.

EXAMPLE 6

Protease (proteolytic acitivity of 4,000,000 [PU]/g, determined in the same manner as in Example 1) obtained from Bacillus sp 0 - 20 as in Example 1 was succinoylated and the enzyme was adsorbed to DEAF-Sephadex (Trade mark, diethylaminoethyl dextran of Pharmacia Fine Chemicals, Sweden) to prepare a water-insoluble enzyme in the following manner.

5 mg of protease was dissolved in 4.5 ml of 0.1 molar concentration borate buffer (containing 0.01 M of $CaCl_2$) at pH 8.0 and 1 mg of succinyl anhydride dissolved in 0.5 ml of dioxan were added to the resulting solution to effect reaction for 30 minutes with stirring. The reaction mixture was dialyzed with 0.005 M of $CaCl_2$ for a day and the dialyzed substance was adsorbed to DEAF-Sephadex (Trade mark, the same as above) which had been buffered with 0.01 molar concentration borate buffer (containing 0.05 M of $CaCl_2$) at pH 8.0 and filled in a column after freeze-drying, 200 mg of water-insoluble enzyme was obtained.

The starting protease (protease-1) and the resultant water-insoluble protease (protease-2) were compared with respect to proteolytic activity and esterolytic activity as follows. The esterolytic activity is expressed in terms of a value when each protease was used in an amount required for exhibiting a proteolytic activity of 100.

| Protease | Proteolytic activity *1) (casein) | Esterolytic activity *2) (acethyl-tyrosine ethyl ester) |
|---|---|---|
| Protease -1 | 100 | 100 |
| Protease -2 | 100 | 1,500 |

*1) Casein-Folin method.
*2) Hesterin method.

Protease-1 and protease-2 were respectively added to 5 ml of blood serum of rabbit such that the activity on acetyl-tyrosine ethyl ester was 500 m M/min as determined by Hesterin method, and reaction was conducted at 37°C for 50 minutes. Anti-infalmmatory substance was separated from the reaction mixture in the following manner.

The serum modified with protease-1 was filtered by using a membrane filter ("Diafilter G-05T," Trade mark, product of Nihon Shinku Gijutsu Co., Ltd., Tokyo, Japan). 5 ml of water was added to the unfiltered liquid for dilution and the diluted liquid was further filtered, whereby 8 ml of filtrate was obtained. The filtrate was concentrated under reduced pressure to obtain 5 ml of a liquid containing an anti-inflammatory substance. (The liquid was free of activity on acetyl-tyrosine ethyl ester and is hereinafter referred to as sample-I).

The blood serum modified with protease-2 was centrifuged at 3,000 r.p.m. for 10 minutes to remove enzyme, whereby 4.5 ml of supernatant was obtained which was diluted with water to prepare a liquid containing an anti-inflammatory substance. (The liquid exhibited no activity on acetyl-tyrosine ethyl ester and is hereinafter referred to as sample-II).

Each of the modified blood serums thus prepared contained peptide, amino acid and sugar and was soluble in water.

On the other hand, 5 ml of rabbit blood serum was left to stand at 37°C for 50 minutes to prepare sample-III for comparison.

Anti-inflammatory effect of these samples was tested. The samples I, II and III were intraperitoneally given to Wister rats, male, weighing about 150 g at a rate of 5 ml/kg (body weight of rat) respectively. In 30 minutes, 0.05 ml of 1% carrageenin was subcutaneously injected in the sole of rear foot of each rat. Increase of volume of the rear foot was measured in 3 hours thereafter. Physiological saline was given in the same manner as above as a control. Inhibition achieved on edema was 62 percent with sample-I and 64 percent with sample-II and no inhibitive effect was achieved with sample-III and with control.

EXAMPLE 7

With 5 ml of blood serum of hen was reacted 100 mg of an insoluble protease (i.e. insoluble chymotrypsin obtained by insolubilizing chymotrypsin by azide method using carboxy-methyl cellulose as will be described later) at 35°C for 50 minutes. The insoluble protease was then removed by filtration to obtain 4.8 ml of filtrate which was free of enzymatic activity. The filtrate contained peptide, amino acid and sugar and was soluble in water but insoluble in methanol.

The filtrate was intraperitoneally given to a rat at a rate of 1 ml/200 g (body weight of rat) to examine its inhibitive effect on edema produced by subcutaneous injection of carrageenin in the heel of rear foot of the rat. In 3 hours after administration, 68 percent inhibition on edema was achieved, without any intraperitoneal bleeding. In contrast, no edema inhibitive effect was seen with administration of blood serum of hen which had not been reacted with insoluble protease.

The insoluble protease mentioned above was prepared in the following manner. Hydrazine was added to methanol solution of carboxymethyl cellulose to prepare a hydrazide of carboxymethyl cellulose, which was reacted with sodium nitrite in a dilute hydrochloric acid solution. The reaction product was then reacted with chymotrypsin at a pH of 8.7 and 5°C with stirring, whereby insoluble chymotrypsin was obtained. The reactive yield of the product was 20 percent in terms of proteolytic activity on casein.

What we claim is:

1. An anti-inflammatory composition which comprises an anti-inflammatorily effective amount of a reaction product of blood serum of cow with a protease obtained from Bacillus sp 0–20, deposit number FERM 270, and an adjuvant, said reaction product being obtained by reacting the serum with the protease at 20 to 60°C for about 0.5 – 5 hours and separating the resultant product from the reaction mixture, and in which said protease is used in an amount ranging from 200 to 2,000γ per ml of the blood serum.

2. An anti-inflammatory composition which comprises an anti-inflammatorily effective amount of a reaction product of blood serum of rat with a protease obtained from Bacillus sp 0–20, deposit number FERM 270, and an adjuvant, said reaction product being obtained by reacting the serum with the protease at 20° to 60°C for about 0.5 to 5 hours and inactivating the enzyme by heating the resultant reaction mixture, and in which said protease is used in an amount ranging from 200 to 2000γ per ml of the blood serum.

3. An anti-inflammatory composition which comprises an anti-inflammatorily effective amount of a reaction product of human serum with bromelin and an adjuvant, said reaction product being obtained by reacting the serum with the bromelin at 20° to 60°C for about 0.5 to 5 hours and separating the resultant product from the reaction mixture, and in which said bromelin is used in an amount ranging from 200 to 2000γ per ml of the blood serum.

4. An anti-inflammatory composition which comprises an anti-inflammatorily effective amount of reaction product of cow blood containing sodium citrate with a protease obtained from Bacillus subtilis and an adjuvant, said reaction product being obtained by reacting the blood with the protease at 20° to 60°C for about 0.5 to 5 hours and separating the resultant product from the reaction mixture, and in which said protease is used in an amount ranging from 200 to 2000γ per ml of the blood.

5. An anti-inflammatory composition which comprises an anti-inflammatorily effective amount of a reaction product of cow serum with a protease obtained from Aspergillus melleus and adjuvant, said reaction product being obtained by reacting the serum with the protease at 20° to 60°C for about 0.5 to 5 hours and separating the resultant product from the reaction mixture, and in which said protease is used in an amount ranging from 200 to 2000γ per ml of the blood serum.

6. An anti-inflammatory composition which comprises an anti-inflammatorily effective amount of a reaction product of blood serum of rabbit with a protease obtained from Bacillus sp 0–20, deposit number FERM 270, and an adjuvant, said reaction product being obtained by reacting the serum with the protease at 20° to 60°C for about 0.5 to 5 hours and separating the resultant product from the reaction mixture, and in which said protease is used in an amount ranging from 200 to 2000γ per ml of the blood serum.

7. An anti-inflammatory composition which comprises an anti-inflammatorily effective amount of a reaction product of blood serum of rabbit with a protease obtained from Bacillus sp 0–20, deposit number FERM 270, and insolubilized by succinoylation and an adjuvant, said reaction product being obtained by reacting the serum with the water-insoluble protease at 20° to 60°C for about 0.5 to 5 hours and separating the resultant product from the reaction mixture, and in which said protease is used in an amount ranging from 200 to 2000γ per ml of the blood serum.

8. An anti-inflammatory composition which comprises an anti-inflammatorily effective amount of a reaction product of blood serum of hen with insoluble chymotripsin and an adjuvant, said reaction product being obtained by reacting the serum with the insoluble chymotripsin at 20° to 60°C for about 0.5 to 5 hours and separating the resultant product from the reaction mixture, and in which said protease is used in an amount ranging from 200 to 2000γ per ml of the blood serum.

* * * * *